United States Patent
Bouillon

[19]

[11] Patent Number: 6,120,759
[45] Date of Patent: Sep. 19, 2000

[54] ANHYDROUS SKIN CLEANSING AGENT AND USE THEREOF

[75] Inventor: Günter Bouillon, Kempen, Germany

[73] Assignee: Chemische Fabrik Stockhausen GmbH, Krefeld, Germany

[21] Appl. No.: 07/750,777

[22] Filed: Aug. 22, 1991

Related U.S. Application Data

[63] Continuation of application No. 07/466,398, filed as application No. PCT/EP88/00963, Oct. 26, 1988.

[30] Foreign Application Priority Data

Oct. 30, 1987 [DE] Germany ............... P3736970

[51] Int. Cl.$^7$ ............... A61K 7/50; A61K 9/10
[52] U.S. Cl. ............... 424/78.31; 510/139; 510/157; 424/499; 424/501
[58] Field of Search ............... 424/78.18, 486–488, 424/499, 501, 78.1, 78.31, 78.37; 510/130, 139, 157, 158

[56] References Cited

U.S. PATENT DOCUMENTS

| | | |
|---|---|---|
| 3,708,426 | 1/1973 | Schrader . |
| 3,956,162 | 5/1976 | Lautenberger ............... 252/168 |
| 4,130,497 | 12/1978 | Oneto et al. ............... 514/786 |
| 4,537,604 | 8/1985 | Dawson ............... 252/174.23 |
| 4,557,853 | 12/1985 | Collins ............... 252/119 |
| 4,612,352 | 9/1986 | Schäfer et al. ............... 524/404 |
| 4,647,396 | 3/1987 | Denzinger et al. ............... 526/271 |
| 4,929,380 | 5/1990 | Schulz et al. ............... 252/95 |

FOREIGN PATENT DOCUMENTS

| | | |
|---|---|---|
| 1949849 | 4/1970 | Germany . |
| 2011156 | 9/1971 | Germany . |
| 3517385 | 5/1984 | Germany . |
| 3736970 C2 | 5/1989 | Germany . |
| 1288805 | 9/1972 | United Kingdom . |

OTHER PUBLICATIONS a. Technical Information Manual, "Aqua Keep", Seitetsu Kagaku Co., Polymer Division.
English Abstract of German Patent: 1949849 (Oct. 2, 1969).
English Abstract and English claims for German Patent: 3736970 (Oct. 30, 1987).
Brochure; "Saniscrub Rubbelcreme", edition 10,000 of Jan. 1987 (D3).
Brochure; "Saniscrub Rubbelcreme", edition 4,000 of Mar. 1990 (D4).
Merck–Index, 10$^{th}$ edition, 1983 (D5).
Lexikon der Hifsstoff, editor H.P. Fiedler, vol. 1,3$^{rd}$ edition reworked and completed 1989 (D6).
Rompp Encyclopedia, 9$^{th}$ edition, vol. 1, 1989 (D7).
Grenzflachenaktive Substanzen, editor S.A. Riethmayer, 20$^{th}$ edition 1969 (D9).
Information Lehman & Voss & Co.
English Abstract of German Patent 2011156 (Mar. 10, 1970).

*Primary Examiner*—Edward J. Webman
*Attorney, Agent, or Firm*—Norris, McLaughlin & Marcus, P.A.

[57] ABSTRACT

An anhydrous skin cleansing agent comprising a surfactant, organic solvent and water-insoluble abrasive as active components and a water-swellable organic polymer as a soil carrier and abrasive.

11 Claims, No Drawings

ANHYDROUS SKIN CLEANSING AGENT AND USE THEREOF

This application is a continuation of application Ser. No. 07/466,398, filed Jul. 27, 1990, which was a 371 of PCT/EP88/00963, filed Oct. 26, 1988.

The present invention relates to a skin cleansing agent, preferably in flowable or pasty state, which comprises water-insoluble but water-swellable solid particles of organic polymers of natural or synthetic origin.

Flowable or paste-like skin cleansing agents are generally used to clean extremely soiled skin areas, e.g., in the metal-working industry or lacquer and varnish factories. Known skin cleaning formulations, in most cases these are pastes, contain surfactants as detergent surfactant, oleophilic and/or oleophobic solutizer, organic solubilizers, and optionally water. These known products furthermore contain as abrasives sand. wood flour, or plastic powder. These solid substances remove the dirt due to their abrasivity. However, they do not prevent that the dissolved or emulsified soil coagulates when it is subsequently dissolved with water and at least partially deposits on the skin again.

It is accordingly the object of the present invention to improve the known skin cleansing agents with respect to their cleansing action, particularly to prevent coagulation and re-deposition of the dissolved or emulsified soil.

This object is achieved by the addition of water-insoluble organic polymers which merely swell in water to a skin cleansing agent comprising surfactants, organic solvents, water-insoluble abrasives, as well as optionally thickeners, builders, perfumes, preserving agents, dyestuffs, antioxidants and/or keratolytic agents.

Thus the subject matter of the present invention is an anhydrous skin cleansing agent comprising surfactants, organic solvents and water-insoluble abrasives, as well as optionally thickeners, builders, perfumes, preserving agents, dyestuffs, antioxidants, and/or keratolytic agents, which skin cleansing agent is characterized by a content of water-insoluble but water-swellable organic polymers.

The water-insoluble but water-swellable polymers are present as solid particles and have the effect of soil carriers in such a way that the dissolved or emulsified soil, on subsequent dilution with water, does not coagulate and redeposit again but is removed. Furthermore, the water-insoluble, water-swellable polymer in the anhydrous formulation may also act as abrasive, and used either as the sole abrasive or in combination with other abrasives known per se. In the anhydrous formulation, the soil encloses the polymer particles which, on subsequent moistening of the hands, extremely swell under absorption of water and prevent coagulation of the dirt and thus resoiling of the skin. In this connection, the water-insolubility of the particles is an absolute precondition. In addition, the solid particles of the polymer, provided that they are not too finely divided, may also act as abrasive in the anhydrous formulation, in that they mechanically remove the impurities due to their abrasivity.

The effect of the water-swellable polymer particles according to the present invention is both novel and surprising:

In DE-A 35 17 385 a cosmetic skin cleansing agent is described which, however, in an anhydrous fatty phase comprises an emulsifier and a water-soluble polymer as abrasive. The water-solubility of the polymer is an absolute precondition that the abrasive can completely be removed from the skin by water. The problem of re-deposition of already removed soil, and thus resoiling of the skin is not mentioned in this publication.

Organic polymers of natural or synthetic origin are used as water-insoluble, but merely swellable solid substances. These may be polymers on the basis of modified natural materials, or on the basis of synthetic products. In general, the water-insolubility is achieved by cross-linking. The term polymers comprises homopolymers as well as copolymers and terpolymers.

Suitable organic polymers on the basis of modified natural products are, for example, products on the basis of starch and cellulose which can be modified by grafting preferably with acrylic derivatives. Examples of acrylic derivatives are (meth-)acrylic acid and the salts thereof. (meth-)acrylonitrile, (meth-)acrylamide, and (meth-)acrylic esters, as well as the partial saponification products of these acrylic derivatives.

Suitable synthetic organic polymers are the homo- and copolymers, particularly of the acrylic derivatives mentioned above, whereby particularly the copolymers among one another or with isobutylene and maleic anhydride are to be mentioned. In addition polyurethanes are suitable, too. The polymers may contain as comonomers acrylamidopropane sulfonic acid, vinylphosphonic acid, vinylsulfonic acid, dialkylaminoalkyl(meth-)acrylates, dialkylamino(meth-)acrylamides, as well as the quaternized forms of the two above mentioned basic comonomers.

In addition to the water-swellable solid particles according to the present invention, known, non-swellable abrasives, such as wood flour, plastic powder, or sand may be used.

As detergent surfactant (surfactants) or emulsifiers the skin cleansing agents according to the present invention preferably comprise alkoxylated fatty alcohols, alkoxylated fatty acids, alkoxylated fatty acid glycerides, alkoxylated alkylphenols or alkylsulfates, alkyl-ether sulfates, sorbitan fatty acid esters, fatty acid glycerides; it is understood that the listed products are not meant to be limitative.

Carboxylic acid esters, paraffinic or isoparaffinic hydrocarbons, arylcarboxylic acid esters or terpenes alone or in mixture among one another are used as solvents in the skin cleansing agent according to the present invention.

As carboxylic acids the esters of alcohols having mono- or polybasic carboxylic acids are used; the alcohols used for this purpose are straight-chain or branched-chain and preferably have 1 to 8 carbon atoms, whereby the lower alcohols having 1 to 4 carbon atoms are preferred. Examples are methanol, ethanol, n-propanol, isopropanol, n-butanol, and isobutanol. As an example of a higher alcohol isooctanol is to be mentioned. The carboxylic acid of the carboxylic acid esters preferably has 1 to 10 carbon atoms and may also be straight- or branched-chain. Examples of carboxylic acids are: formic acid, acetic acid, propionic acid as monobasic acids, as well as adipic acid, sebacic acid, or citric acid as polybasic acids. Examples of suitable carboxylic acid esters are the low carboxylic acid esters known as solvents, such as butylacetate, or higher-boiling derivatives, e.g., methoxy butylacetate.

As thickeners and builders waxes, cellulose derivatives (e.g. cellulose ether), synthetic polymers, fumed silica, and modified bentonites are used.

The cleansing agents according to the present invention may in addition comprise perfumes, preserving agents, grease-restoring agents, dyestuffs, and/or antioxidants.

The quantity ratios of the components may vary within wide ranges. The content of water-insoluble, but water-swellable polymer particles amounts to 0.3 to 55. preferably 0.1 to 17.6, in particular 1 to 12.5%-wt, relative to the total weight of detergent surfactant (surfactant), solvent and water-swellable polymer.

Taking the same basis as for the water-swellable polymer, the content of solvent amounts to 5 to 99, preferably 20 to 98, and in particular 30 to 70%-wt., and that of detergent surfactant (surfactants) amounts to 0.7 to 94.7%-wt, preferably 1.4 to 79.4, and in particular 29 to 69%-wt.

The amount of further, optionally present components, such as thickeners, grease-restoring agents, perfumes, preserving agents, dyestuffs, antioxidants, and keratolytic agents, which may be present alone or in admixture, amounts to 0 to 90%-wt. relative to the total formulation.

The particle size of the water-swellable solid particles is smaller than 1,000 μm, preferably smaller than 500 μm when used as soil carrier and abrasive; e.g., the grain size is in the range of about 50 to 400 μm. If the water-swellable polymer is merely used as soil carrier alone or in combination with other abrasives known per se, the particle size is smaller and is in the order of smaller than 200 μm, preferably in the order of smaller than 150 μm, particularly smaller than 100 μm, e.g., in the range of 10 to 200 μm. Corresponding size fractions are suitably obtained by screening.

The present invention will be illustrated further by the following examples.

| Formulation I | |
| --- | --- |
| 15 %-wt | oleic acid neutralized with triethanol-amine (detergent surfactant) |
| 58 %-wt | butylacetate (solvent) |
| 5 %-wt | soy oil (grease-restoring agent) |
| 5.1 %-wt | pryrogenic silicic acid (thickener) |
| 0.4 %-wt | perfume |
| 9 %-wt | polymer component a (according to table I) |
| 7.5 %-wt | polyethyl powder, grain size smaller than 300 μm |

| Formulation Ia | |
| --- | --- |
| 15 %-wt | nonylphenol 9 EO |
| 36 %-wt | iso-hexadecane |
| 55 %-wt | polymer component a (according to table I) smaller than 100 μm |

In order to demonstrate the different cleansing action between water-soluble and merely water-swellable abrasives in the case of polymers, a standard formulation (formulation II) was developed, and equal amounts of polymer components (table I) having the same particle size were incorporated into each of the following formulations.

Formulation used:

| Formulation II: | |
| --- | --- |
| 16.2 %-wt | fatty alcohol 12/18 5 EO (detergent surfactant) |
| 59.5 %-wt | ester mixture (solvent) |
| 5.4 %-wt | grease-restoring agent (fatty acid alkyl-ester) |
| 14.2 %-wt | thickener (3.4%-wt. pryrogenic silicic acid; 7%-wt. ethyleneglycol distearate; 3.8%-wt. cellulose acetate butyrate) |
| 0.4 %-wt | perfume |
| 4.3 %-wt | polymer components a to f according to table I |
| 100 % | |

TABLE I

As polymer components were used:

| Trade name: | | |
| --- | --- | --- |
| a = Favor SAB 422 | water-swellable | cross-linked polyacrylic acid, partially neutralized |
| b = Rhodopol 23 | water-soluble | xanthan gum, heteropolysaccharide |
| c = Aqua-Keep | water-swellable | see a) |
| d = Praestol 2530 | water-soluble | linear acrylamide-sodium acrylate-copolymer |
| e = Natrosol | water-soluble | hydroxyalkyl cellulose |
| f = Sunwet IM 1000 | water-swellable | acrylic acid-modified starch |

Formulations a to f thus obtained were tested with respect to their cleansing action according to the following hand-wash-test:

Description of the method

Hand-wash-test

1. Material and Method 1.1. Test material 1.1.1. Lacquer (red); quick-drying lacquer on the basis of fish oil; manufacturer Messrs. Rust Oleum 1.2. Test persons As test persons a group of six male, dermally healthy persons at the age of 20 to 60 was chosen.

It is a precondition that all test persons have a palm skin structure which is caused by manual work.

1.3 Test quantities

A defined amount of typical dirt (or lacquer) and the amount of test substance is determined before the test starts.

1.4. Assessment scheme

Assessment is carried out after washing according to a 0–5 points-scale. The degree of residual impurities on the palm of the hand is assessed.

0=clean
1=slight residual soil
2=medium residual soil
3=considerable residual soil
4=extreme residual soil
5=no cleansing effect 1.5. Performance In the morning and in the afternoon the following washing is carried out using one product each:

0.5 ml test soil (cf. 1.1.1.) is applied to the palm and shortly rubbed into the skin allowed to dry for 3 minutes 0.5 ml of the test product is applied and shortly rubbed into the skin approximately 1 ml water is added; washing for 20 seconds rinsing under running, cold water assessment of the cleansing effect according to the 5-points-scale The results thus obtained are shown in table II:

TABLE II

| Product/test person | a | b | a | c | a | d | a | e | a | f |
|---|---|---|---|---|---|---|---|---|---|---|
| 1 | 2.5 | 4.5 | 2 | 3 | 2 | 3.5 | 1 | 1.5 | 1.5 | 2 |
| 2 | 3 | 4 | 3 | 4 | 2.5 | 4 | 2 | 2.5 | 2 | 2 |
| 3 | 2.5 | 4.5 | 3 | 2.5 | 3.5 | 4 | 2.5 | 2 | 2.5 | 2.5 |
| 4 | 3 | 4.5 | 3.5 | 2.5 | 2.5 | 4 | 2 | 2.0. | 5 | 2.5 |
| 5 | 3 | 3.5 | 2 | 3 | 2 | 3 | 2 | 3 | 1.5 | 2 |
| 6 | 3 | 4.5 | 3 | 3.5 | 4 | 3.5 | 1.5 | 2 | 1.5 | 1 |
| φ | 2.8 | 4.3 | 2.8 | 3.1 | 2,8 | 3.7 | 1.8 | 2.2 | 1.6 | 2 |

Test II

In this test it was tested whether the increased cleansing effect was maintained with additional incorporation of a common insoluble and non-swellable abrasive (polyethylene powder was chosen). For this purpose, a certain amount of water-soluble or water-swellable polymer having the same particle distribution was incorporated into a standard formulation comprising 7.5% polyethylene powder, the cleansing effect was then tested.

Formulation III

| | |
|---|---|
| 15 %-wt. | fatty alcohol $C_{12}$–$C_{18}$ 5 EO (detergent surfactant) |
| 9.3 %-wt. | dimethyl adipate ⎫ |
| 36.3 %-wt. | dimethyl glutarate ⎬ (solvent) |
| 9.4 %-wt. | dimethyl succinate ⎭ |
| 5 %-wt. | isooctyl stearate (grease-restoring agent) |
| 2.3 %-wt. | fumed silica ⎫ |
| 7 %.wt. | ethyleneglycol distearate ⎬ (thickener) |
| 3.8 %-wt. | cellulose acetate butyrate ⎭ |
| 0.4 %-wt. | perfume |
| 4.0 %-wt. | polymer components a, c, d, or f (according to table I smaller than 45 μm) |
| 7.5 %-wt. | polyethylene powder smaller than 300 μm |

The results obtained are shown in table III

TABLE III

| Product/Test person | f | a | c | a | d | a |
|---|---|---|---|---|---|---|
| 1 | 2 | 1 | 0.5 | 1 | 3 | 0.5 |
| 2 | 1 | 1 | 1 | 1 | 3 | 1.5 |
| 3 | 1.5 | 1.5 | 1 | 1.5 | 2.5 | 1.5 |
| 4 | 1.5 | 1 | 1.5 | 2 | 3 | 1 |
| 5 | 1.5 | 1 | 1 | 1 | 2.5 | 2 |
| 6 | 0.5 | 1 | 1.5 | 2 | 2 | 1.5 |
| φ | 1.3 | 1.1 | 1.1 | 1.4 | 2.7 | 1.3 |

Test III

Test III shows that a considerable amount of cleaning product can be saved, if the polymer according to the present invention is used, i.e., the soil carrying capacity is superior.

Formulation as in test II; 0.5 ml of the product according to the present invention with polymer component a compared to 1 ml of the product not claimed by the present invention with polymer component d was used for washing.

The results obtained are shown in table IV

TABLE IV

| Product/Test person | a (0.5 ml) | d (1.0 ml) |
|---|---|---|
| 1 | 1 | 1.5 |
| 2 | 1 | 1.5 |
| 3 | 1 | 2 |
| 4 | 0.5 | 1 |
| 5 | 1 | 1.5 |
| 6 | 1 | 2 |
| φ | 0.9 | 1.6 |

Formulation IV

| | Formulation A | Formulation B | Formulation C | Formulation D | Formulation E |
|---|---|---|---|---|---|
| Fatty alcohol $C_{12}$–$C_{18}$ 5 EO | 15 g | 15 g | 15 g | 15 g | 15 g |
| Dimethyl adipate | 9.3 g | 9.3 g | 9.3 g | 9.3 g | 9.3 g |
| Dimethyl glutarate | 36.3 g | 36.3 g | 36.3 g | 36.3 g | 36.3 g |
| Dimethyl succinate | 9.4 g | 9.4 g | 9.4 g | 9.4 g | 9.4 g |
| Aerosil | 5.0 g | 5.0 g | 5.0 g | 5.0 g | 5.0 g |
| Polyethylene powder smaller 315 μm | 7.5 g | — | — | — | — |
| Favor smaller 315 μm | — | 7.5 g | — | — | 17.5 g |
| Favor smaller 45 μm | — | — | — | 4.0 g | 4.0 g |

TABLE V

Hand-wash-test:
Amount of product: 0.5 ml

| Test person | 0.5 ml lacquer A | 0.3 ml lacquer B | 0.5 ml C | 0.7 ml lacquer D | lacquer A | lacquer E |
|---|---|---|---|---|---|---|
| 1 | 1.0 | 0.5 | 3.0 | 2.5 | 1.5 | 1.0 |
| 2 | 1.0 | 0.5 | 2.0 | 2.0 | 1.0 | 0.5 |
| 3 | 0.5 | 0 | 3.0 | 1.0 | 1.0 | 0.5 |
| 4 | 0 | 0.5 | 1.5 | 1.0 | 1.0 | 0.5 |
| 5 | 0.5 | 0.5 | 2.5 | 2.0 | 1.5 | 1.0 |
| X | 0.6 | 0.4 | 2.4 | 1.7 | 1.2 | 0.7 |

Test A compared to B: abrasive PE compared to abrasive FAVOR
→no considerable difference; in case of this particle size the soil carrying capacity does scarcely take effect.
Test C compared to D: without abrasive (FAVOR used as soil carrier)
→soil carrying capacity can clearly be recognized.
Test A compared to E: abrasive PE compared to abrasive PE and soil carrier FAVOR
→soil carrying capacity becomes evident even in abrasive-containing formulations.
Summary:
The washing tests carried out clearly show the superiority of water-insoluble, but water-swellable polymers (Favor SAB, Sunwet IM 1000, Aqua-Keep) compared to water-soluble polymers (test I). Test II shows that the superiority of these polymers is maintained, even if a common abrasive is incorporated. The degree of improvement achieved by a polymer according to the present invention used in combination with a common abrasive becomes evident in test III. Although half of the cleansing product was used, an improved cleaning effect was achieved, compared to the full amount of product which comprises a water-soluble polymer.

What is claimed is:

1. An anhydrous skin cleansing agent comprising by weight 0.7 to 94.7% of a surfactant, 5 to 99% of an organic solvent, and 0.3 to 55% of a water-swellable organic polymer as a soil carrier and abrasive, and optionally a water-insoluble abrasive, the organic solvent comprising a member selected from the group consisting of carboxylic acid esters, paraffinic or isoparaffinic hydrocarbons, arylcarboxylic acid esters, terpenes and mixtures thereof.

2. A skin cleansing agent according to claim 1, further containing at least one member selected from the group consisting of a thickener, builder, grease-restoring agent, perfume, preserving agent, dyestuff, antioxidant and keratolytic agent.

3. A skin cleansing agent according to claim 1, wherein the water-swellable organic polymer is present in about 0.3 to 55% by weight of the total weight of surfactant, solvent and water-swellable organic polymer.

4. A skin cleansing agent according to claim 1, wherein the water-swellable organic polymer comprises a member selected from the group consisting of poly(meth)-acrylic acid or a salt thereof, a graft copolymer of an acrylic compound with starch, a graft copolymer of an acrylic compound with cellulose, a saponification product of poly(meth-)acrylonitrile, a (meth-)acrylamide, an acrylic ester, a polyurethane, and mixtures thereof.

5. A skin cleansing agent according to claim 1, wherein the water-swellable organic polymer contains monomer units selected from the group consisting of acrylamidopropane sulfonic acid, vinylphosphonic acid, vinylsulfonic acid, a dialkyl aminoalkyl(meth-)acrylate, a dialkyl aminoalkyl (meth-)acrylamide, a quaternization form of a dialkyl aminoalkyl(meth-)acrylate and a quaternization form of a dialkyl aminoalkyl(meth-)acrylamide.

6. A skin cleansing agent according to claim 1, wherein the surfactant comprises a selected from the group consisting of an alkoxylated fatty alcohol, alkoxylated fatty acid, alkoxylated fatty acid glyceride, alkoxylated alkylphenol, alkyl sulfate, alkyl ether sulfate, sorbitan fatty acid ester, a fatty acid glyceride, and mixtures thereof.

7. A skin cleansing agent according to claim 1, wherein the solvent comprises a member selected from the group consisting of an ester of a mono- or polybasic carboxylic acid having 1 to 10 carbon atoms with an alkanol having 1 to 8 carbon atoms, a paraffinic or isoparaffinic hydrocarbon, an aryl carboxylic acid ester, a terpene, and mixtures thereof.

8. A skin cleansing agent according to claim 1, further containing as a thickener or builder a member selected from the group consisting of a cellulosic compound, fumed silica, a modified bentonite, a wax, and mixtures thereof.

9. A skin cleansing agent according to claim 1, wherein the particle size of the water-swellable organic polymer is less than 1,000 $\mu$m.

10. A skin cleansing agent according to claim 1, wherein, and the particle size of the water-swellable organic polymer is less than 200 $\mu$m.

11. In the cleansing of the skin wherein a skin cleansing agent and water are applied to the skin, the improvement which comprises employing as the skin cleansing agent an agent according to claim 1.

* * * * *